US009706974B2

(12) United States Patent
Schliermann (10) Patent No.: US 9,706,974 B2
(45) Date of Patent: Jul. 18, 2017

(54) SELECTING MEASUREMENT FIELDS FOR AN X-RAY EXAMINATION (71) Applicant: Claus-Günther Schliermann, Kemnath (DE)

(72) Inventor: Claus-Günther Schliermann, Kemnath (DE)

(73) Assignee: Siemens Aktiengesellschaft, München (DE)

( * ) Notice: Subject to any disclaimer, the term of this patent is extended or adjusted under 35 U.S.C. 154(b) by 351 days.

(21) Appl. No.: 14/325,112

(22) Filed: Jul. 7, 2014

(65) Prior Publication Data

US 2015/0010129 A1    Jan. 8, 2015

(30) Foreign Application Priority Data

Jul. 8, 2013    (DE) .................... 10 2013 213 313

(51) Int. Cl.
*A61B 6/00* (2006.01)
*G01N 23/04* (2006.01)

(52) U.S. Cl.
CPC ........... *A61B 6/542* (2013.01); *G01N 23/043* (2013.01)

(58) Field of Classification Search
CPC .... A61B 6/00; A61B 6/04; A61B 6/08; A61B 6/542; A61B 6/545; G01N 23/043
See application file for complete search history.

(56) References Cited

U.S. PATENT DOCUMENTS

| 7,769,137 B2 | 8/2010 | Maack et al. |
| 2003/0165216 A1* | 9/2003 | Walker ............... A61B 6/544 378/108 |
| 2004/0156473 A1 | 8/2004 | Nonaka et al. |
| 2006/0239410 A1 | 10/2006 | Schutz |
| 2006/0265307 A1 | 11/2006 | Walker, Jr. |
| 2007/0025525 A1 | 2/2007 | Gilath |

(Continued)

FOREIGN PATENT DOCUMENTS

| CN | 101052351 A | 10/2007 |
| CN | 101472523 A | 7/2009 |

(Continued)

OTHER PUBLICATIONS

German Office Action dated Mar. 12, 2014 for corresponding German Patent Application No. DE 10 2013 213 313.8 with English translation.

(Continued)

*Primary Examiner* — Hoon Song
(74) *Attorney, Agent, or Firm* — Lempia Summerfield Katz LLC (57) ABSTRACT

Selection of at least one measurement field of a measurement chamber formed with a plurality of measurement fields, for dose monitoring when making an x-ray recording of an object is provided. A subset of measurement fields from the plurality of measurement fields of the measurement chamber is predetermined by selecting an orientation of the object. Measurement fields not belonging to the subset of measurement fields are blocked for the selection. At least one measurement field is set for dose monitoring when making an x-ray recording of the object by selecting measurement fields from the subset of measurement fields.

17 Claims, 5 Drawing Sheets (56) References Cited

U.S. PATENT DOCUMENTS

2007/0242806 A1* 10/2007 Borgmann .............. A61B 6/08
378/207
2009/0122960 A1   5/2009 Maack et al.
2009/0180590 A1   7/2009 Borgmann et al.

FOREIGN PATENT DOCUMENTS

| DE | 102005003225 A1 | 7/2006 |
| EP | 1440660 A2 | 7/2004 |
| JP | 2013005862 A | 1/2013 |
| WO | 2006-038165 A1 | 4/2006 |
| WO | 2007-148262 A1 | 12/2007 |
| WO | WO2012057046 A1 | 5/2012 |

OTHER PUBLICATIONS

"Optimale Patientenpositionierung in der Radiographie durch Videou," Abstract, http://ip.com/IPCOM/000207924, pp. 1-2, 2013.
Chinese office Action for related Chinese Application No. 201410317460.7 dated Aug. 3, 2016, with English Translation.
Chinese Office Action for Chinese Patent Application No. 201410317460.7 mailed Apr. 12, 2017 with English translation.

\* cited by examiner

SELECTING MEASUREMENT FIELDS FOR AN X-RAY EXAMINATION

This application claims the benefit of DE 10 2013 213 313.8, filed on Jul. 8, 2013, which is hereby incorporated by reference in its entirety.

BACKGROUND

The present embodiments relate to selecting at least one measurement field of a measurement chamber for dose monitoring when making an x-ray recording of an object.

In x-ray technology, a situation that regularly arises is that a utilized amount of radiation or x-ray dose in the case of x-ray examinations is to stay within a desired value range in order to provide a high image quality of the x-ray image. In the case of a dose that is too low, underexposed x-ray recordings are obtained, while a dose that is too high would lead to overexposure. If the dose lies outside of the work range, either the amount of light or energy generated at the outlet is too low, and the images obtained do not have a sufficiently high quality for medical diagnostics, or else the amount of dose is too high. In the case of a dose that is too high, changes in the dose, caused by differing absorption of the tissue of the radiation patient, are no longer converted into a proportional change in the light or energy signal. The generated images then likewise may not be used for medical diagnostics due to the lack of contrast.

It is for this reason that an automatic exposure control (AEC) may be used in x-ray technology. AEC is described, for example, in the document 2007/0025525 A1. Such an automatic exposure control or such an AEC system may be connected to every modern generator and is already available in many devices. Measurement detectors in the region of the image receiver surface provide the x-ray generator with a switch-off signal after reaching the required dose. By way of example, ionization chambers, photomultipliers or semiconductor radiation receivers are used as measurement detectors. The measurement detectors may be arranged in a measurement chamber and form measurement fields in the measurement chamber. Previously, work was generally undertaken with measurement chambers that have three measurement fields (e.g., a three-chamber system).

Figure 2:
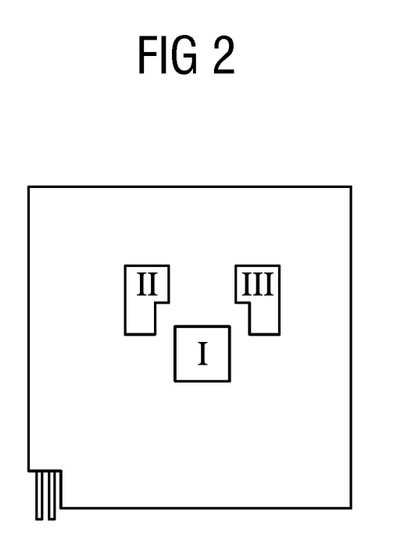
FIG. 2 shows one embodiment of a three-field measurement chamber.

The arrangement of these three measurement fields in a three-chamber system is shown in, for example, FIG. 2 of the present application or in FIGS. 1a and 1b of US 2007/0025525 A1. When examining a patient, the measurement chamber is aligned with the organ or body part to be examined. Specific measurement fields for the automatic exposure control are then used depending on organ or body part. There are specific stipulations for the medical practitioner as to which measurement fields are to be used for which examination. By way of example, if the head is examined, only the central measurement chamber I from FIG. 2 may be used, while all three measurement chambers are used in, for example, a pelvic examination. Therefore, there is a relatively fixed predetermined relationship in the medical literature between the organ or body part and the measurement chamber or chambers of a three chamber measurement system to be used. This is used in organ programs, in which there may be an automatic selection of measurement chambers.

Figure 4:
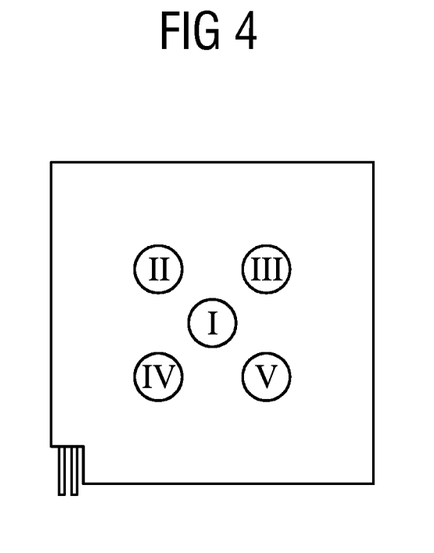
FIG. 4 shows one embodiment of a five-field measurement chamber.

In a recent development, measurement chambers with a larger number of measurement fields are used. One new system is the five-chamber system. By way of example, such a system is shown in FIG. 4. A five-chamber system or a five-field measurement chamber has a symmetric design. In this chamber, at most three fields are used (e.g., the assignment of organ or body part to employed chamber, as is conventional in medicine, continues to be used in principle). An advantage of the five-field measurement chamber is that if the orientation of the patient is changed, this is not accompanied by a change in the orientation of the measurement chamber, but rather, the correct orientation of the measurement chamber is provided by selecting the at most three measurement fields to be used. By way of example, if the measurement chamber in FIG. 2 is provided for vertical orientation of the patient, the measurement chamber would be co-rotated in the case of rotation of the patient in the horizontal direction. This is not provided for in many systems, and x-ray recordings may thus only be made for one orientation of the patient.

These restrictions do not apply to the five-field measurement chamber from FIG. 4. By way of example, the measurement fields I, II and III may be used in the case of a vertical orientation of the patient, while use would be made of the measurement chamber triplet I, III and V or I, II and IV in the case of a vertical orientation. Therefore, there is no longer any need to rotate the measurement chamber, or x-ray recordings for different patient orientations become possible.

However, the use of measurement chambers with more than three fields (e.g., the use of five-field measurement chambers) also harbors difficulties. As a result of the larger number of possibilities, there is an increased risk of the incorrect measurement chambers being selected. In general, an incorrect selection leads to an incorrect exposure. As a result of this, the generated images become useless. Therefore, attempts have been made to provide a safer operation. Thus, it has been proposed to project (e.g., by light) the position of the selected measurement fields (e.g., the contours thereof) onto the patient in order thus to supply the user with feedback about the correctness of the selected chambers. By way of example, such systems are described in US 2007/0025525 A1 and in WO 2007/148262 A1. By way of example, the publication "Optimale Patientenpositionierungen in der Radiographie durch Videounterstützung [Ideal patient positioning in radiography by means of video assistance]" (see http://ip.com/IPCOM/000207924) also describes a camera system that establishes the location of the patient relative to the measurement fields of an AEC chamber from the image of the camera with the aid of pattern recognition algorithms.

SUMMARY AND DESCRIPTION

The proposed solutions discussed above have two deficits. First, the solutions still have a certain susceptibility to errors (e.g., if the user does not consider this optical feedback or interprets the optical feedback incorrectly). Second, the solutions are comparatively complicated systems that lead to increased costs and higher complexity.

The scope of the present invention is defined solely by the appended claims and is not affected to any degree by the statements within this summary.

There is a need for a low-complexity safety system, with a high safety factor, against incorrect selections of measurement fields of a measurement chamber. The present embodiments may obviate one or more of the drawbacks or limitations in the related art. For example, a low-complexity safety system against incorrect selections of measurement fields of a measurement chamber is provided.

Selection is within the meaning of a stipulation.

According to one or more of the present embodiments, a selection of at least one measurement field (e.g., 1 to 3 measurement fields) of a measurement chamber formed with a plurality of measurement fields (e.g., five or seven measurement fields) is provided for dose monitoring or dose regulation when making an x-ray recording of an object (e.g., patient or workpiece to be examined). In the process, an orientation of the object is selected for the x-ray recording. The term "selection" may, in this case, also include an automatic stipulation based on system parameters. In one embodiment, an orientation is selected from a restricted selection of selectable orientations (e.g., horizontally or vertically and, in the case of these two directions, optionally also a further distinction between the two directions in accordance with the location of the patient's head). A subset of measurement fields (e.g., three measurement fields) from the plurality of measurement fields of the measurement chamber is predetermined by selecting or choosing the orientation. The measurement fields not belonging to the subset of measurement fields may no longer be selected as measurement fields to be used, or the selection is blocked for these measurement fields. Stipulating measurement fields for dose monitoring is brought about by selecting measurement fields from the subset of measurement fields. In one embodiment, the subset of measurement fields includes the measurement fields that may be provided for the x-ray recording in view of the orientation of the object. By way of example, in this way, a three-field measurement chamber situation may be emulated by a five-field measurement chamber after selecting the orientation. In one embodiment, only the subset of measurement fields is displayed on a display (e.g., touchscreen) of an operating unit for selecting at least one measurement field. In contrast thereto, measurement fields not belonging to the subset of measurement fields may be blocked for selection in this configuration by virtue of these measurement fields not being displayed for selection on the display of the operating unit. Thus, for example, blocking is realized via the blocked measurement images not being selectable on the display.

As a result of the present embodiments, the situation of selecting measurement fields from a set of measurement fields that are all possible for the measurement, which the operating staff is used to, may be established. By way of example, this is how the situation of a three-field measurement chamber is emulated for a five-field measurement chamber such that the operating staff may make the selection that was conventional in the past. This provides a higher operational safety that is greater than the above-described methods for display on a patient, to the extent that measurement fields that are not possible for the examination may not even be selected. This solution has very little complexity, since merely a two-step selection process (e.g., first orientation and then measurement fields) are to be realized (e.g., by software including instructions executed by a processor).

In accordance with one development, the operating comfort may be increased further by displaying the subset of measurement fields on the display of the operating unit being brought about in accordance with the selected orientation of the object or the illustration of information about the selected orientation. Additional illustration of information about the selected orientation may occur on the display or surface used for the operation. In one embodiment, a symbol or symbols for the subset of measurement fields are oriented in this configuration such that correspondence with the direction of the orientation of the object, or the selected orientation, is provided.

The selection, according to one or more of the present embodiments, of an orientation of the object may be brought about, for example, by an entry of an operating person or automatically in accordance with an orientation of the object, registered by at least one sensor. In a development, a combination of a selection in accordance with an orientation of the object, registered by at least one sensor, and an entry of an operating person may also be provided (e.g., within the meaning of a correction or adaptation of the automatic selection by the user).

An x-ray system for making x-ray recordings of an object is also provided. The x-ray system includes an operating unit, adapted according to one or more of the present embodiments, and at least one sensor for registering an orientation of the object. The x-ray system may be configured to transmit the registered position to the operating unit for the purposes of predefining a subset of measurement fields from the plurality of measurement fields of the measurement chamber for the selection of a measurement chamber.

The system may be developed such that the orientation of the object is adapted in accordance with the orientation selection undertaken for the selection of the measurement fields. By way of example, this is brought about with the aid of a positioning system for making x-ray recordings of an object, which, in addition to the operating unit, also includes a mounting device (e.g., patient couch) for the object. The mounting device may be aligned with respect to the orientation (e.g., rotatable patient mount). The positioning system also includes a control unit (e.g., a processor) for adapting the orientation of the object by aligning the mounting device in accordance with the selected orientation.

DETAILED DESCRIPTION

Figure 1:
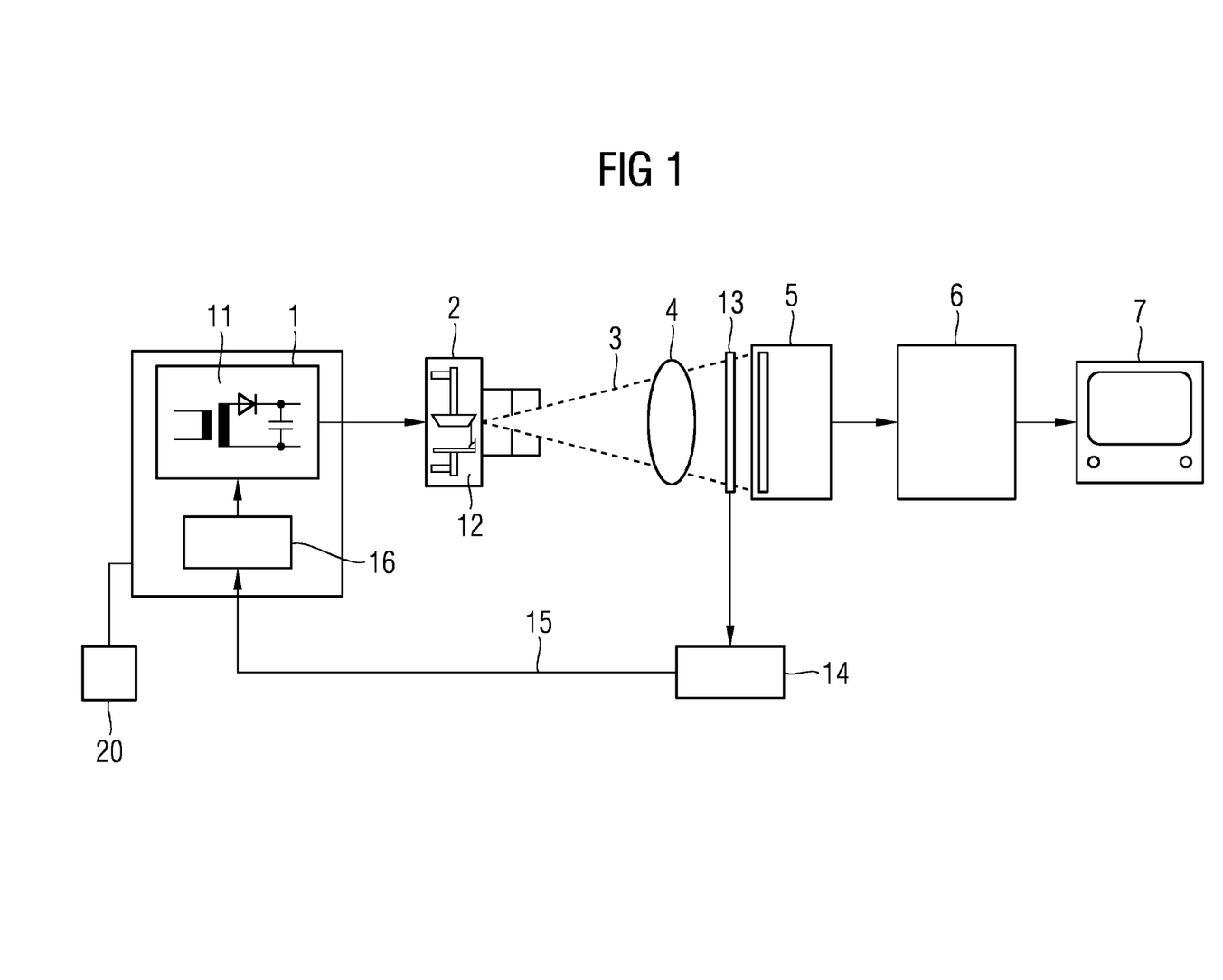
FIG. 1 shows one embodiment of an x-ray system with automatic exposure control.

FIG. 1 shows one embodiment of an x-ray diagnostics apparatus. The x-ray diagnostics apparatus includes a high-voltage generator 1, to which an x-ray emitter 2 is attached in a height-adjustable manner. The emitter 2 generates x-ray beams 3 that penetrate an object 4 situated in a beam path of the x-ray beams 3. Arranged subsequently in the beam path is an x-ray detector 5 that is connected to an image system 6 is linked to a monitor 7 for reproducing the registered x-ray images. The image system 6 may include a computer, a transducer, an image storage medium and processing circuits. An operating element or operating console 20 that includes an input interface and thus enables a control of the x-ray diagnostics apparatus is also provided.

A dose regulation using automatic exposure control (AEC) for individual images is provided. FIG. 1 shows this control loop (e.g., AEC) for generating an individual image. A dose measurement chamber 13 is arranged upstream of the x-ray detector 5. The dose measurement chamber 13 is linked to measurement electronics 14 that generate an AEC actual signal 15 that is fed to AEC regulation electronics 16 arranged in the high-voltage generator 1.

FIG. 2 shows a conventional three-field measurement chamber with three fields I, II and III. Previously, automatic x-ray exposure controls were often designed with such three measurement fields. The three measurement fields were fixedly assigned to the patient orientation. A different patient orientation (e.g., rotated by 90° or 180°) was not possible with these arrangements or required the simultaneous rotation of the measurement chamber. The operating units for these three-field controls may be achieved such that the three fields may be selected or deselected individually by three pushbuttons. The assignment between measurement fields and patient orientation is unambiguous in this case (e.g., left-middle-right). This type of operation was introduced on the market many years ago, and the operating staff is acquainted therewith.

Figure 3:
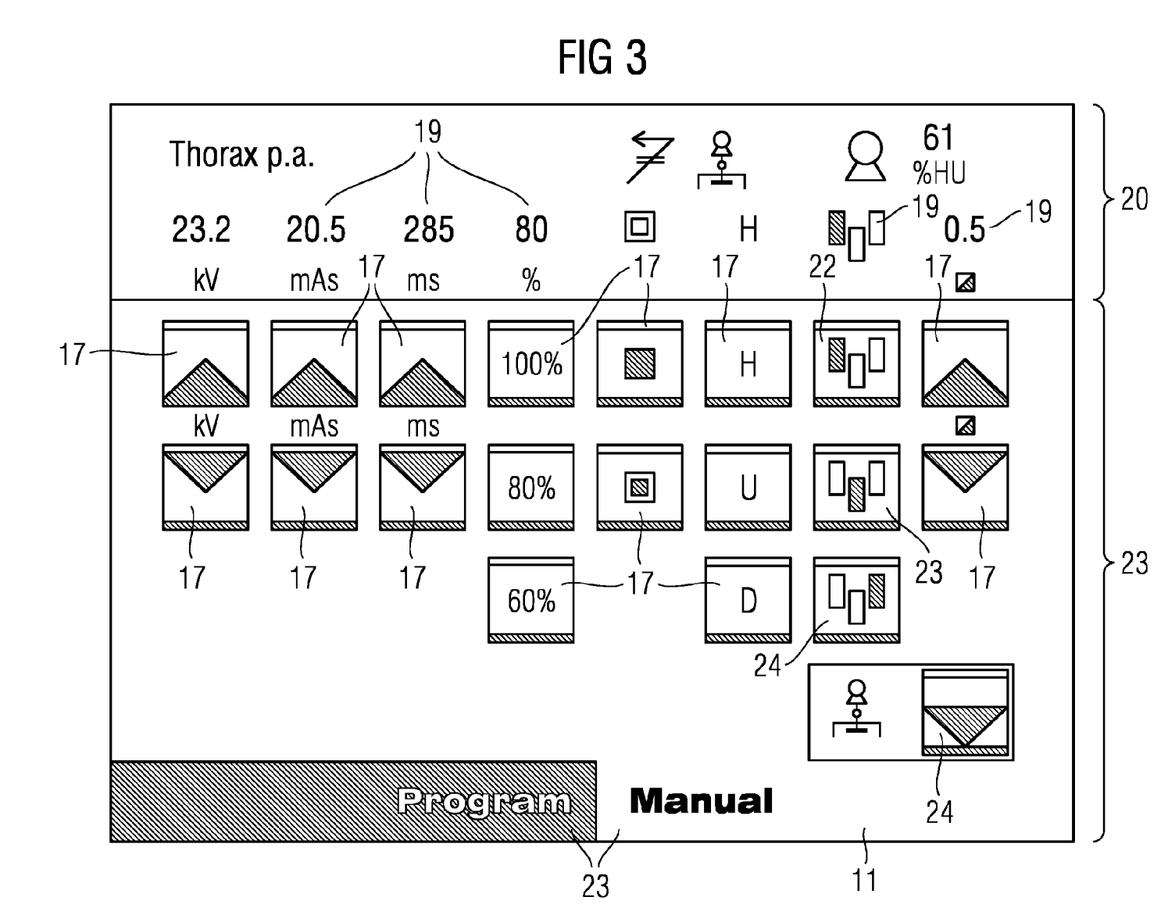
FIG. 3 shows one embodiment of a display of an operating element for an x-ray device.

By way of example, this also becomes clear on the basis of FIG. 3, which shows a typical display of an operating element for an x-ray emitter with a row of setting pushbuttons 17 and items of setting information 19. By way of example, this display is realized by a screen that, in an operating region 21, is configured as a touchscreen for selecting settings. This operating region 21 includes three pushbuttons 22, 23 and 24 for selecting measurement fields of a three-field measurement chamber. The measurement field selectable by the respective pushbutton is illustrated in FIG. 3 in dark on the pushbutton. Settings are displayed in an information region 20.

Figure 5:
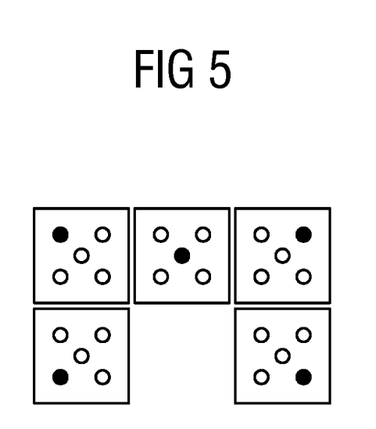
FIG. 5 shows a conventional operation in the case of a five-field measurement chamber.

The patient orientation may be selected freely with the introduction of symmetric five-field measurement chambers (FIG. 4). However, if the operating unit from three-field exposure control units is simply extended to five fields, there is a high risk of incorrect operation because the operator is also to take account of the patient orientation when selecting the measurement field. This may be understood based on FIG. 5, where the operating unit is configured such that the five measurement fields may be selected individually. The operator is to think about the orientation of the patient in order to select the correct fields. This is a starting point for one or more of the present embodiments.

Figure 6:
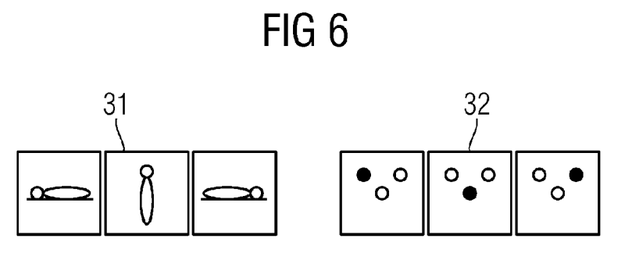
FIG. 6 shows a two-step operation according to one embodiment using orientation selection and subsequent field selection.
Figure 7A:
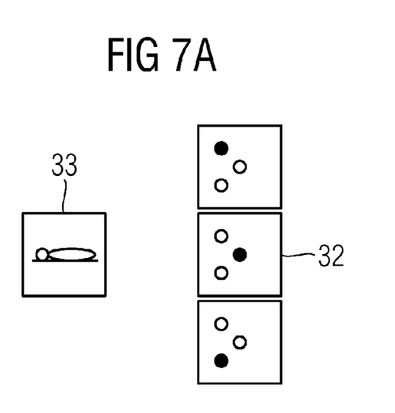
FIGS. 7a, b and c show different exemplary displays that take into account the selected orientation when displaying the fields.
Figure 7B:
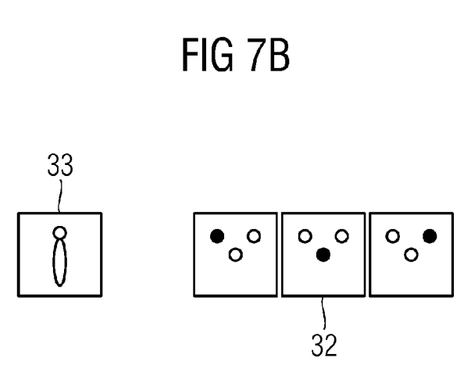
Figure 7C:
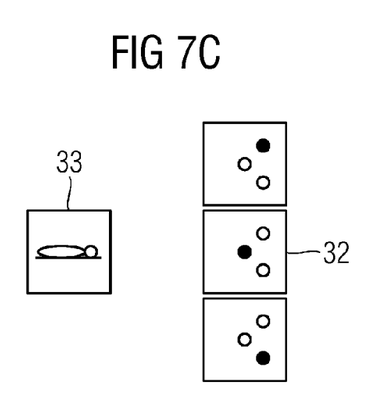

As shown in FIG. 6, the operation takes place in two steps, which is reflected in pushbuttons for the orientation selection 31 and pushbuttons 32 for the field selection. These pushbuttons 31 and 32 may be displayed simultaneously or successively on the operating unit for selection. The pushbuttons 31 set the patient orientation with respect to the measurement chamber. In the present case, one vertical orientation and two horizontal orientations are provided. The second part of the fields 32 allows individual selection and deselection of three measurement fields, which are used for the examination. The operation of this second part of the selection pushbuttons 32 is the same as the operation of a three-field exposure control unit and therefore leads to a well-known situation for the operating staff.

In one development (FIG. 7), the second part of the fields 32 is shown in accordance with the selected orientation. The direction of the fields depicted on the pushbuttons is shown in the same direction as the head of the patient in accordance with the selected orientation 33. This pushbutton illustration of the pushbuttons 32 is even more suggestive than in FIG. 6. In accordance with one configuration, the orientation of the patient is established automatically by sensors, and appropriate measurement chambers are predetermined. In this case, the orientation pushbuttons 31 from FIG. 6 may not need to be displayed. Pushbuttons for selecting the measurement chambers may be displayed to the user immediately. This may likewise be brought about like in FIG. 7 (e.g., by displaying a symbol 33 for the established orientation and by displaying measurement chamber selection pushbuttons 32 with an appropriate illustration).

Within the scope of this invention, the number of possible patient orientations may be restricted (e.g., discrete selection by pushbuttons; a patient may lie on an x-ray table with the head only toward the right or left, but may not lie obliquely). This may be predetermined by the instrument geometry. Alternatively, a system that corrects the actual patient setting in accordance with the selection options in the first part of the operating unit (e.g., via the location of the patient in accordance with the selected orientation being corrected) is provided.

The exemplary embodiments are explained in the medical setting. However, this is only one of many options for use. In general, the one or more of the present embodiments may be used in any x-ray-technical system (e.g., in the field of material science).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for selecting at least one measurement field of a measurement chamber formed with a plurality of measurement fields, for dose monitoring when making an x-ray recording of an object, the method comprising:
   selecting an orientation of the object from a plurality of predetermined orientations;
   predetermining a subset of measurement fields from the plurality of measurement fields of the measurement chamber based on the selected orientation;
   blocking measurement fields of the plurality of measurement fields not belonging to the subset of measurement fields for the selection; and
   specifying at least one measurement field of the plurality of measurement fields for dose monitoring when making an x-ray recording of the object, the specifying comprising selecting measurement fields from the subset of measurement fields.

2. The method of claim 1, further comprising displaying the subset of measurement fields on a display of an operating unit for selecting at least one measurement field from the subset of measurement fields.

3. The method of claim 2, wherein, within the blocking of the measurement fields not belonging to the subset of measurement fields, the measurement fields not belonging to the subset of measurement fields are not displayed for selection on the display of the operating unit.

4. The method of claim 2, wherein the displaying of the subset of measurement fields on the display of the operating unit comprises displaying the subset of measurement fields in accordance with the selected orientation of the object or an illustration of information about the selected orientation.

5. The method of claim 1, wherein selecting the orientation of the object comprises selecting the orientation of the object by an entry of an operating person selecting the orientation of the object, automatically in accordance with the orientation of the object registered by at least one sensor, or a combination thereof.

6. The method of claim 2, wherein the orientation of the object is adapted in accordance with the selected orientation.

7. An operating unit for selecting at least one measurement field of a measurement chamber formed with a plurality of measurement fields, for dose monitoring when making an x-ray recording of an object, the operating unit comprising:
 a processor configured to:
  select an orientation of the object from a plurality of predetermined orientations;
  select a subset of measurement fields from the plurality of measurement fields of the measurement chamber based on the selected orientation;
  block selection of measurement fields of the plurality of measurement fields not belonging to the subset of measurement fields; and
  specify at least one measurement field of the plurality of measurement fields for dose monitoring when making an x-ray recording of the object, the specification comprising selection of measurement fields from the subset of measurement fields.

8. The operating unit of claim 7, further comprising a display for displaying the subset of measurement fields.

9. The operating unit of claim 8, wherein within the blocking, the operating unit does not display, on the display of the operating unit, the measurement fields not belonging to the subset of measurement fields for the selection of the measurement fields.

10. The operating unit of claim 8, wherein the operating unit is configured to display the subset of measurement fields in accordance with the selected orientation of the object or for illustration of information about the selected orientation.

11. The operating unit of claim 9, wherein the operating unit is configured to display the subset of measurement fields in accordance with the selected orientation of the object or for illustration of information about the selected orientation.

12. An x-ray system for making x-ray recordings of an object, the x-ray system comprising:
 an operating unit for selecting at least one measurement field of a measurement chamber formed with a plurality of measurement fields, for dose monitoring when making an x-ray recording of the object, the operating unit comprising:
  a processor configured to:
   select an orientation of the object from a plurality of predetermined orientations;
   select a subset of measurement fields from the plurality of measurement fields of the measurement chamber based on the selected orientation;
   block selection of measurement fields of the plurality of measurement fields not belonging to the subset of measurement fields; and
   specify at least one measurement field of the plurality of measurement fields for dose monitoring when making an x-ray recording of the object, the specification comprising selection of measurement fields from the subset of measurement fields; and
 at least one sensor operable to register an orientation of the object.

13. The x-ray system of claim 12, wherein the x-ray system is configured to transmit the registered orientation to the operating unit for predefining the subset of measurement fields from the plurality of measurement fields of the measurement chamber for selection of the measurement chamber.

14. The x-ray system of claim 12, further comprising:
 a mounting device for the object, the mounting device being alignable with respect to the orientation of the object; and
 a control unit configured to adapt the orientation of the object by aligning the mounting device in accordance with the selected orientation.

15. The x-ray system of claim 12, wherein the operating unit further comprises a display for displaying the subset of measurement fields.

16. The x-ray system of claim 15, wherein within the blocking, the operating unit does not display, on the display, the measurement fields not belonging to the subset of measurement fields for the selection of the measurement fields.

17. The x-ray system of claim 15, wherein the operating unit is configured to display the subset of measurement fields in accordance with the selected orientation of the object or for illustration of information about the selected orientation.

* * * * *